US011209413B2

(12) United States Patent
Kahn et al.

(10) Patent No.: US 11,209,413 B2
(45) Date of Patent: Dec. 28, 2021

(54) METHOD FOR DETERMINING HARDNESS CONCENTRATION USING A MONOVALENT ION SELECTIVE ELECTRODE

(71) Applicant: Ecowater Systems LLC, Woodbury, MN (US)

(72) Inventors: Malcolm Kahn, Franklin Lakes, NJ (US); Robert Astle, Middlefield, CT (US); Jeffrey Zimmerman, Forest Lake, MN (US)

(73) Assignee: Ecowater Systems LLC, Woodbury, MN (US)

( * ) Notice: Subject to any disclaimer, the term of this patent is extended or adjusted under 35 U.S.C. 154(b) by 77 days.

(21) Appl. No.: 16/369,682

(22) Filed: Mar. 29, 2019

(65) Prior Publication Data

US 2019/0302086 A1 Oct. 3, 2019

Related U.S. Application Data

(60) Provisional application No. 62/649,932, filed on Mar. 29, 2018.

(51) Int. Cl.
  *G01N 33/18* (2006.01)
  *G01N 27/333* (2006.01)
  *C02F 1/42* (2006.01)

(52) U.S. Cl.
  CPC ......... *G01N 33/1853* (2013.01); *C02F 1/42* (2013.01); *G01N 27/333* (2013.01);
  (Continued)

(58) Field of Classification Search
  CPC .......... G01N 33/1853; G01N 33/1813; G01N 33/1893; G01N 27/333; G01N 27/3335;
  (Continued)

(56) References Cited

U.S. PATENT DOCUMENTS 3,246,759 A * 4/1966 Matalon ............... B01J 49/85
  210/96.1
3,383,310 A * 5/1968 Ammer ................ B01J 49/85
  210/662

(Continued)

FOREIGN PATENT DOCUMENTS

WO 1987000286 A1 1/1987
WO WO-8700286 A1 * 1/1987 .......... G01N 33/492

*Primary Examiner* — Joshua L Allen
(74) *Attorney, Agent, or Firm* — DeLio Peterson & Curcio LLC; Robert Curcio

(57) ABSTRACT

A method of application to provide a workable solution for tracking the hardness of water utilizing an ion selective electrode by tracking the relative hardness of water at the outflow or egress of an ion exchange column. A monovalent cation exchange membrane (ion selective electrode) distinguishes hard water and softened water in a water flow stream. A voltage is applied across the membrane, facilitating the movement of sodium though the membrane (such that anions and divalent ions are excluded), and the current is measured. The change in current (delta current) is used to determine the hard water concentration or level of hardness in an influent stream. A second application estimates or detects the exhaustion of an ion exchanger, and/or determines the regeneration time/cycle of the ion exchanger through the use of an ion selective membrane. Blending of the influent hard water and effluent soft water allows a user to control hardness levels of the effluent.

16 Claims, 3 Drawing Sheets

(52) U.S. Cl.
CPC ..... *G01N 33/1813* (2013.01); *G01N 33/1893* (2013.01); *C02F 2209/055* (2013.01); *C02F 2303/16* (2013.01)

(58) Field of Classification Search
CPC ... C02F 1/42; C02F 2209/055; C02F 2303/16
See application file for complete search history.

(56) References Cited

U.S. PATENT DOCUMENTS

| | | | | |
|---|---|---|---|---|
| 4,257,887 | A * | 3/1981 | Rak | B01J 49/85 210/140 |
| 4,797,192 | A * | 1/1989 | Takiguchi | G01N 27/28 204/412 |
| 5,022,980 | A * | 6/1991 | Tanaka | G01N 27/4165 204/400 |
| 6,814,872 | B2 | 11/2004 | Rawson | |
| 2004/0104175 | A1 * | 6/2004 | Rawson | B01J 49/85 210/662 |
| 2008/0161665 | A1 | 7/2008 | Ye | |
| 2008/0302651 | A1 * | 12/2008 | Arai | C02F 1/46109 204/157.15 |
| 2010/0301882 | A1 * | 12/2010 | Socknick | G05D 21/02 324/694 |
| 2011/0132818 | A1 | 6/2011 | Dopslaff et al. | |
| 2012/0118762 | A1 * | 5/2012 | Bakker | G01N 27/333 205/789 |
| 2015/0122668 | A1 | 5/2015 | Karabin | |
| 2019/0336960 | A1 * | 11/2019 | Balidas | B01J 47/14 |

\* cited by examiner

METHOD FOR DETERMINING HARDNESS CONCENTRATION USING A MONOVALENT ION SELECTIVE ELECTRODE

BACKGROUND OF THE INVENTION

1. Field of the Invention

The present invention relates to a method of application to provide a workable solution for tracking the hardness of water. More specifically, it relates to the utilization of an ion selective electrode and operational method for measuring the influent hardness as well as tracking and controlling the relative hardness of water at the outflow or egress of an ion exchange column with precision and accuracy. There is a well known thermodynamically favored reaction, or ion exchange, wherein ion exchange resin in the predominantly monovalent cation form exchanges two monovalent cations for every divalent cation removed from the fluid stream. Thus, by monitoring the relative levels of the influent and effluent concentrations of the monovalent cations in question, the influent hardness can be determined. Additionally, a feedback control can be used in conjunction with a blending valve to control the amount of hardness in the effluent.

2. Description of Related Art

Water systems using groundwater as a source are generally concerned with water hardness, since as water moves through soil and rock it dissolves small amounts of naturally-occurring minerals and carries them into the groundwater supply. Water is a great solvent for calcium and magnesium, so if the minerals are present in the soil around a water-supply well, the hard water may be delivered to homes. Water hardness varies as a function of geography. For example, in areas within the United States where the water is relatively hard, industries might have to spend money to soften their water, as hard water can damage equipment. Hard water can even shorten the life of fabrics and clothes.

Furthermore, incoming hardness may fluctuate due to changes in blending of different water sources. For example, in the winter a ground water source may be used and in the summer a surface water source may be used. The hardness is most likely different. Additionally, a municipality generally has more than one well. The wells have different hardness concentrations. Depending on which well is supplying water the hardness in the source water delivered to a water softener will fluctuate. This makes for appreciable variations in feed water hardness.

Calcium and magnesium dissolved in water are the two most common minerals that make water "hard." The degree of hardness becomes greater as the calcium and magnesium content increases and is related to the concentration of multivalent cations dissolved in the water.

The hardness of water is generally quantified by three types of measurements: grains per gallon, milligrams per liter (mg/L), or parts per million (ppm). General guidelines for classification of waters are typically: 0 to 60 mg/L (milligrams per liter) of calcium carbonate is classified as soft; 61 to 120 mg/L is classified as moderately hard; 121 to 180 mg/L is classified as hard; and more than 180 mg/L is classified as very hard.

The table below depicts the general hardness classification categories of water:

| Grains Per Gallon | Milligrams Per Liter (mg/L) or Parts Per Million (ppm) | Classification |
|---|---|---|
| 0-3.5 | 0-60 | Soft to Slightly Hard |
| 3.5-7.0 | 60-120 | Moderately Hard |
| 7.0-10.5 | 120-180 | Hard |
| over 10.5 | over 180 | Very Hard |

Hard water may form deposits that clog plumbing. These deposits, referred to as "scale", are composed mainly of calcium carbonate ($CaCO_3$), magnesium hydroxide ($Mg(OH)_2$), and calcium sulfate ($CaSO_4$). Calcium and magnesium carbonates tend to be deposited as off-white solids on the inside surfaces of pipes and heat exchangers. This precipitation (formation of an insoluble solid) is principally caused by thermal decomposition of bicarbonate ions but also happens in cases where the carbonate ion is at saturation concentration. The resulting build-up of scale restricts the flow of water in pipes. In boilers, the deposits impair the flow of heat into water, reducing the heating efficiency and allowing the metal boiler components to overheat. In a pressurized system, this overheating can lead to failure of the boiler.

The presence of ions in an electrolyte, in this case, hard water, can also lead to galvanic corrosion, in which one metal will preferentially corrode when in contact with another type of metal, when both are in contact with the electrolyte.

Conductivity is a measure of water's capability to pass electrical flow. This ability is directly related to the concentration of ions in the water. These conductive ions come from dissolved salts and inorganic materials such as alkalis, chlorides, sulfides, and carbonate compounds. The more ions that are present, the higher the conductivity of water. Likewise, the fewer ions that are in the water, the less conductive it is. Distilled or deionized water can act as an insulator due to its very low (if not negligible) conductivity value. In contrast, sea water has a very high conductivity.

Conductivity can also be a measure for total dissolved solids (TDS). Total dissolved solids combine the sum of all ionized particles that are generally smaller than 2 microns. This includes all of the disassociated electrolytes that make up salinity concentrations, as well as other compounds such as dissolved organic matter. The higher the level of TDS (ppm), the higher the degree of water hardness (1 grain of hardness is approximately 17.1 ppm (mg/L) in TDS). This means that the measure of conductivity directly correlates to the measure of ions that contribute to water hardness.

In North America and many other countries, the water quality changes seasonally as sources are changed or weather conditions change. Thus, while a customer sets up or performs the initial softener commissioning step in order for the softener to optimally perform at the hardness measured during the installation, any subsequent changes in the feed water will result in poor performance—either the customer will periodically get untreated water or they will have poor water and salt efficiencies.

Many consumers use water softeners to soften the water used in their homes, the work place, schools, etc. These water softeners are typically preset to soften water of a predefined degree of hardness.

A water softener includes a resin tank that is filled with resin comprising small beads of cross-lined polystyrene sulfonic acid, and is generally referred to as a cation resin. The resin is usually placed into service with $Na^+$ ions on the beads. When hardness ions come into contact with the $Na^+$ ions bound to the resin, they exchange, or the calcium displaces two Na+ ions, and the Na$^+$ ions are released in the water.

One problem realized with water hardness in general is the time-variant change of hardness in feed water, such as city feed water. This can be attributed to such configurations as having feed water combined from multiple sources with each source having a different hardness level.

Different methods in the art have been used to measure calcium. For example, in U.S. Pat. No. 6,814,872 issued to Rawson on Nov. 9, 2004 titled "CONTROLLER AND METHOD FOR CONTROLLING REGENERATION OF A WATER SOFTENER," a water hardness indicator is taught in form of calcium ion selective electrode. However, it does not teach measuring hardness as a function of divalent elements such as magnesium, barium, strontium, etc., present in hard water (in flow) and which contribute to water hardness.

SUMMARY OF THE INVENTION

Bearing in mind the problems and deficiencies of the prior art, it is therefore an object of the present invention to provide an apparatus and method for measuring differential sodium in a water flow, and determine total hardness therefrom.

It is another object of the present invention to implement a methodology using a sodium ion selective electrode to quantify more precisely total hardness considering all divalent elements present in hard water.

It is yet another object of the present invention to provide feedback control of the system through the utilization of a blending valve.

Still other objects and advantages of the invention will in part be obvious and will in part be apparent from the specification, and which are directed to a method to determine the total hardness in a fluid stream comprising: introducing an ion exchange column or vessel in monovalent cationic form, the column or vessel having an inlet and an outlet, herein the inlet receives a fluid stream; providing monovalent cation selective electrodes positioned at the inlet of the vessel, and at the outlet of the vessel, respectively; measuring monovalent cation concentration by a first signal output from the monovalent cation selective electrode positioned at the inlet of the column or vessel; measuring monovalent cation concentration by a second signal output from the monovalent cation selective electrode positioned at the output of the column or vessel; calculating a differential monovalent concentration; and calculating a hardness value from the differential monovalent concentration.

The method further includes connecting one of the monovalent cation selective electrodes to a fluid path with one or more valves designed to introduce feed water or softened water to the monovalent cation selective electrodes.

The method may also include mixing a fraction of hard water stream with a fraction of the softened water stream using at least one blending valve.

The blending valve may be implemented to adjust the hardness of the water at the ion exchange column or vessel output.

The monovalent cation selective electrodes are preferably of the cation selected from the group of elements comprising hydrogen, sodium, or potassium.

The method may include monitoring sodium levels downstream until the sodium levels approach influent concentrations indicating a complete breakthrough of hardness.

The ion exchange column or vessel in monovalent cationic form may include an ion specific electrode (ISE) sensor comprising three chambers, wherein a first chamber includes a working electrode in contact with a conductive solution and an ionophore membrane barrier, a second chamber includes a reference electrode in contact with potassium chloride (KCl) solution and bound by a dialysis membrane, and a third chamber is located between the ionophore membrane and the dialysis membrane where sample fluid can be introduced for measurement, such that electrical continuity exists from the working electrode, through the conductive solution, the ionophore membrane, the sample fluid, the dialysis membrane, and the KCl solution, to the reference electrode.

In a second aspect, the present invention is directed to a method to determine the total hardness in a fluid stream comprising: providing an ion exchange column or vessel in monovalent cationic form, the column or vessel having an inlet and outlet, wherein a fluid stream is connected to the inlet of the ion exchange column; measuring monovalent cation concentration from a signal output of a monovalent cation selective electrode positioned at the inlet of the ion exchange column; employing a valve mechanism to redirect fluid flow, such that the valve mechanism directs feed water to the monovalent cation selective electrode for a first sodium measurement, and directs softened water to the monovalent cation selective electrode for a second sodium measurement; and determining the influent hardness by measuring the differential monovalent cation concentration.

This method may include: a) connecting the monovalent cation selective electrode to a fluid path with one or more valves designed to introduce feed water or softened water to the monovalent cation selective electrode; b) mixing a fraction of hard water with a fraction of a stream of the softened water using at least one blending valve in the ion exchange column; and/or c) adjusting hardness of the water at the output of the ion exchange column.

In a third aspect, the present invention is directed to a method for controlling hardness in a fluid stream comprising: introducing an ion exchange column or vessel in monovalent cationic form, the column or vessel having an inlet and an outlet; providing monovalent cation selective electrodes positioned at the inlet of the vessel, and at the outlet of the vessel, respectively; performing a first sodium measurement on an initial influent fluid stream (Na+in-initial); performing a second sodium measurement on an initial effluent fluid stream (Na+out-initial); measuring a differential monovalent concentration from the first and second sodium measurements; determining a total hardness value (TH) proportional to the influent fluid stream via the differential monovalent concentration such that $Na^+_{out-initial} - Na^+_{in-initial} \propto TH$; performing a third sodium measurement ($Na^+_{out-blend}$) downstream of a blending valve, the blending valve blending the influent fluid stream with the effluent fluid stream; determining the amount of total hardness removed ($TH_{removed}$) from a differential measurement of the third sodium measurement ($Na^+_{out-blend}$) and the first sodium measurement on the initial influent fluid stream ($Na^+_{in-initial}$) such that $Na^+_{out-blend} - Na^+_{in-initial} \propto TH_{removed}$; and calculating hardness in the effluent fluid stream ($H_{effluent}$) from the difference of the total hardness (TH) and the total hardness removed ($TH_{removed}$) such that $H_{effluent} = TH - TH_{removed}$.

In a fourth aspect, the present invention is directed to a method of determining regeneration of a water softener comprising: providing a first monovalent cation selective electrode positioned at the inlet of an incoming feed water line for the water softener; measuring a first hardness value from the first monovalent cation selective electrode; providing a second monovalent cation selective electrode positioned within a tank of the water softener; measuring a second hardness value from the second monovalent cation selective electrode; calculating a differential monovalent concentration from the first and second hardness values measured; and determining a regeneration limit of a resin bed in the water softener based on the calculated differential monovalent concentration.

This method may further include: a) locating a point of consumed resin in the water softener; b) determining a breakthrough measurement point to yield a determination of spent resin without measuring total (actual) hardness; and/or c) predicting future regeneration by calculating time from the regeneration limit, as measured in gallons-before-regeneration.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
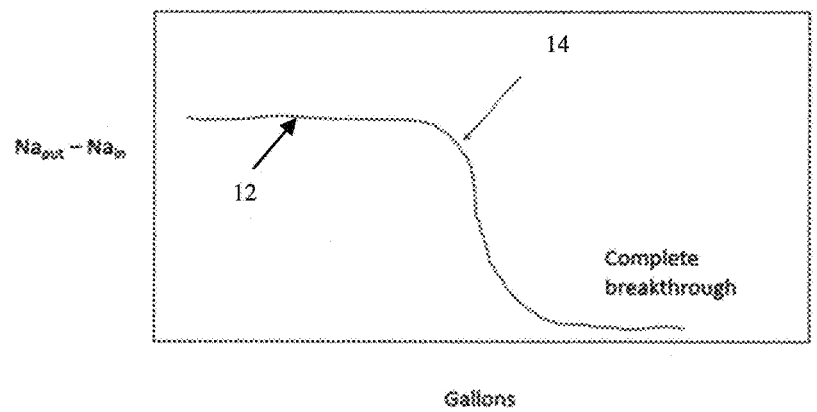
FIG. 1 graphically depicts the breakthrough point as a knee in the curve graphing the differential in sodium ion outflow and sodium ion inflow ($Na^+_{effluent} - Na^+_{influent}$) as a function of water flow (in gallons)

In describing the preferred embodiment of the present invention, reference will be made herein to FIGS. 1-6 of the drawings in which like numerals refer to like features of the invention.

The present invention utilizes an ion specific electrode insomuch as it is beneficial to have a monitor that can adjust the hardness measurement value in-situ (real time) after the commissioning step, when the water conditions change. Essentially, in-situ monitoring of water hardness is performed by continuously measuring the sodium ion concentration for water at inlet and outlet of a softener using a sodium ion-selective electrode.

An ion selective electrode (or ISE) is a transducer (or sensor) that converts the activity of a specific ion dissolved in a solution into an electrical potential, which can be measured by a volt meter or pH meter. The voltage is theoretically dependent on the logarithm of the ionic activity. Normally, the sensing electrode has a flat membrane imbedded with a specific ion sensitive material. An ideal ISE would consist of a thin membrane across which only the intended ion could be transported.

The membrane is in contact with an internal electrode conductor element, such as for example Ag—AgCl, connected to the electrode lead, which is connected to the pH or concentration meter. The voltage, which will develop for the ISE electrode, is a function of the ion sensitive membrane. Response of the electrode may be described as the voltage developed between the inside and the outside of the ion sensitive membrane. The ion sensitive membrane composition will determine the electrode's response time and its sensitivity to other ions.

An ISE works on the basic principal of a galvanic cell. By measuring electric potential generated across a membrane by "selected" ions, and comparing it to a reference electrode, a net charge is determined. The strength of this charge is directed proportional to the concentration of the selected ion.

The sensing part of the electrode is usually made from an ion specific membrane, coupled together with a reference electrode (either separate or in combination). Many ISE's incorporate their own reference electrode; these are usually either a single junction refillable type Ag/AgCl type, or a double junction type, which is used for ISE's such as chloride, bromide, and the like. These types of reference electrodes allow the user to select an appropriate electrolyte for the particular application. For instance, potassium nitrate is commonly used as a filling solution for ISE's such as Chloride, Bromide, Iodide, Cyanide, Silver, and Sulfide.

The hardness via the measurement process using an ISE may be validated against standard EDTA titration, which is a known and established method (as per EPA guidelines) for determination of water hardness.

The proposed methodology requires a measure of hardness that can be both robust and inexpensive compared to existing technology, which in the present instance employs specific ion electrode measurements. The electric potential produced by an ISE is theoretically dependent on the logarithm of the ion activity, as described by the Nernst Equation:

$$E = (2.3026)*(RT/zF)*\log(A)$$

where

R is the universal gas constant (8.314472 $JK^{-1}$ $mol^{-1}$)

F is the Faraday constant, the number of coulombs per mole of electrons, (9.64853399($10^4$) C $mol^{-1}$)

T is temperature (kelvins)

z is the number of electrons transferred in the cell reaction

A is the ratio of ions outside the cell to ions inside the cell

The sensing part of the electrode is made from the ion specific membrane, coupled together with a reference electrode (either separate or as a combination). Ion-selective electrodes are used where measurements of ionic concentration in an aqueous solution are required.

In support of a hardness measurement, an electrolytic cell is presented that can drive current or ions in solution across a membrane or plurality of membranes that are preferential to the passage of monovalent cations (versus multivalent cations), and prevent the passage of anions.

The process is based upon the determination of Na ion ($Na^+$) concentrations by sodium ion selective electrodes. The invention is based on the principle of a cation exchanger where the divalent ions present in feed water are exchanged with $Na^+$ ions of the exchanger. The outflow contains a $Na^+$ ion concentration that is the sum of original $Na^+$ present in the feed water and $Na^+$ ion generated, represented by the relationship of 2 $Na^+$ for each $Ca^{2+}$, $Mg^{2+}$, $Ba^{2+2}$, or $Sr^{2+}$, as a result of the ion exchange. For example, each sodium ion exchanged replaces two hardness ions of the feed water: $Na^+_{exchanged} = 2\ Ca^{+2}_{feed}$.

Thus, the total hardness can be calculated by the differential sodium (when the sodium based ion exchange column is newly regenerated), and the total hardness (TH) (measured in moles per liter) as:

$$CaCO_{3(TH)} = ([Na^+]_{effluent} - [Na^+]_{influent})/2$$

where the respective sodium concentrations are in moles per liter.

When the ion exchange capacity tends to get exhausted, less divalents are exchanged as less $Na^+$ ions are available in the ion exchanger, at which point the concentration of $Na^+$ ion at out flow decreases. Complete exhaustion of the ion exchange column occurs when there are no more $Na^+$ ions available to exchange the divalents. Hence, the $Na^+$ concentration drops to the $Na^+$ ion concentration of in flow (feed water). Thus, for a complete ion exchanger life cycle, the difference between $Na^+$ concentrations at the outflow and inflow varies from maximum to near zero.

In one embodiment of implementing a hardness measurement, a sodium ion selective electrode is fixed at the in-flow of the ion exchanger column, and another is fixed at the outflow. For the regenerated/fresh ion exchange column in the sodium form, the differential sodium can be used to calculate the total hardness in the feed water, where $$\Delta Na\ mg/L/(7.866\ mg\ monovalent\ cation/gpg\ total\ hardness).$$

In this manner, the softener may then update the operating parameters to predict when to regenerate the bed based on the gallons of water treated.

Alternatively, the system could be monitored until the downstream sodium levels approach influent concentrations, indicating a complete breakthrough of hardness through the bed.

FIG. 1 graphically depicts the breakthrough point as a knee 14 in the curve 12 graphing the differential in sodium ion outflow and sodium ion inflow ($Na^+_{effluent} - Na^+_{influent}$) as a function of water flow (in gallons). Complete breakthrough is depicted when the difference between $Na^+_{effluent} - Na^+_{influent}$ is close to zero.

In a second embodiment employing the methodology of the present invention, a single ion exchange electrode and a valve mechanism is utilized. This embodiment provides for: a) feed (hard) water to the sensor for a sodium measurement; b) softened water to the sensor for a sodium measurement; and c) the calculation of the differential between the measured sodium and total hardness.

This technique can be performed at any time when there is ample ion exchange capacity in the resin tank.

Another method embodiment of the present invention may be designed such that the system will not only measure hardness, but also be useful for control of a custom hardness level in the water provided to a home. This is especially advantageous, for example, in Europe where consumers prefer a specific level of hardness (typically, 3 gpg) in the water provided to the home.

In this embodiment, a sodium measurement is performed first on the feed (hard) water, and then on the softened water to determine the total hardness of the influent water flow, $TH_{influent}$, via a differential measurement.

Subsequently, a sodium measurement can then be taken downstream of a blending valve to measure and control the total hardness. The logical progression of the measurements is as follows:

$$(Na^+_{out-initial} - Na^+_{in-initial}) \propto TH$$

$$(Na^+_{out-blend} - Na^+_{in-initial}) \propto TH_{removed}$$

$$\text{Hardness in Effluent} = TH - TH_{removed}$$

Essentially, the present invention may be simplified as a methodology for determining total hardness in a fluid stream utilizing an ion exchange column in a monovalent cationic form having an inlet and an outlet, where one or more monovalent ion selective electrodes are positioned either at the inlet, outlet, or at both locations simultaneously.

A monovalent cation selective electrode is in fluid communication with one or more valves incorporated within a fluid path in order to introduce feed water or softened water to the monovalent cation selective electrode. Additionally, one blending valve may be incorporated in the ion exchange column to allow a fraction of the feed (hard) water to mix with a fraction of the softened water. In this manner, the blending valve may be utilized to adjust the hardness of the water at the output.

Preferably, the monovalent cation selective electrode (ion specific electrode) is one of a cation selected from the group of elements comprising hydrogen, sodium, or potassium. Sodium is presented in the description below as an exemplary embodiment; however, the other aforementioned elements may be used without compromising the differential methodology presented.

An ion specific electrode (ISE) typically presents millivolts output for a given element (ion) concentration. In one embodiment, the sensor comprises three chambers: (1) a working electrode in contact with a conductive solution and with an ionophore membrane barrier, (2) a reference electrode in contact with KCl and bound by a dialysis membrane, and (3) a chamber between the two membranes where sample fluid can be introduced for measurement and dispensed, and such that there is electrical continuity from the working electrode, through the conductive solution, the ionophore membrane, the sample fluid for analysis, the dialysis membrane, the KCl, and to the reference electrode. Feed water is fed into the chamber, where sodium is measured, then soft water is introduced into the sensor and sodium measured. The ISE produces a voltage that correlates to the concentration of the relevant monovalent ion. The voltage is used to determine the true concentration of the ion.

Performing a differential measurement technique using a monovalent cation selective electrode opens up applications for other ISE elements, such as hydrogen, potassium, etc., for industrial applications in addition to the water softener commercial application provided herein.

A preferred method to determine the total hardness in a fluid stream is performed by measuring a differential monovalent concentration, and includes the following steps: a) introducing an ion exchange column or vessel in the monovalent cationic form with an inlet and outlet, where the inlet receives a fluid stream; b) measuring monovalent cation concentration by a signal output from the monovalent cation selective electrode(s) positioned at the inlet of the column or vessel; c) measuring monovalent cation concentration by a signal output from the monovalent cation selective electrode(s) positioned at the output of the column or vessel; and d)

determining the influent hardness by calculating the differential monovalent cation concentration.

The method is further enhanced by connecting the monovalent cation selective electrode(s) to a fluid path having one or more valves designed to introduce feed water or softened water to the electrode(s). In addition, the method step of blending a fraction of the hard water with a fraction of the softened water may also be performed with the introduction of a blending valve. Through the incorporation of a blending valve, a further method step may include adjusting the hardness of the water at the output.

Figure 2:
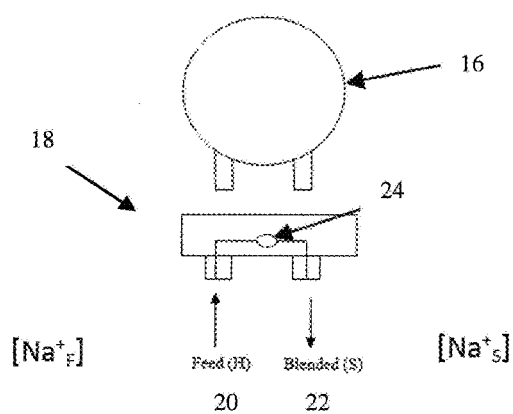
FIG. 2 depicts a water softener apparatus incorporating a monovalent cation selective electrode having a feed (hard) water input and a soft water output, which may also be a blended water output.

FIG. 2 depicts a water softener apparatus 16 incorporating a monovalent cation selective electrode 18, having a feed (hard) water input 20, and a soft water output 22 which may also be a blended water output depending upon the utilization of blending valve 24.

Using this apparatus, the total hardness is measured via a hard water measurement and a soft water measurement. The system is capable of controlling (opening and closing) the blending valve 24. The differential $Na^+$ is measured from the difference in the feed water and the blended water (with hardness removed). Thus, $[Na^+_f]-[Na^+_s]=[Na^+]_{Exchanged}$. For every two sodium ions (2 $Na^+$), one hardness ion is exchanged. The sodium is measured first in the inlet and outlet with the blending valve closed to obtain a true feed hardness. Subsequent measurements can be taken with the blending valve opened and compared to the original measurement to determine the actual hardness in downstream of the blending valve.

Figure 3:
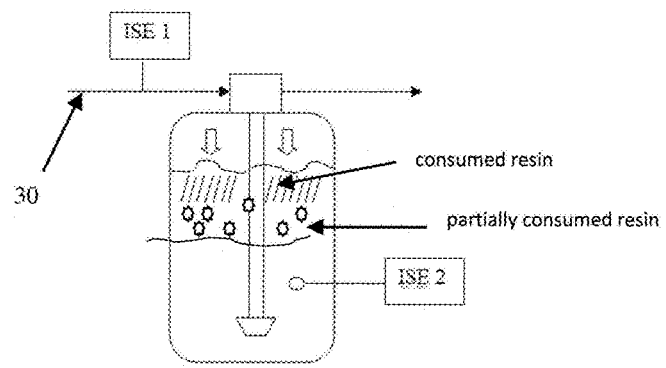
FIG. 3 depicts a methodology that uses a water softener configuration having two ion specific electrodes (ISE 1, ISE 2)

FIG. 3 depicts a methodology that uses a water softener configuration having two ion specific electrodes (ISE 1, ISE 2). The first ion specific electrode (ISE 1) is placed at the incoming ingress line 30 for the feed water. The second ion specific electrode (ISE 2) is placed within the water softener tank. In this configuration, the differential measurement allows for a determination of when regeneration may be required.

This dual ISE configuration can be used to locate the point of consumed resin. A breakthrough measurement can yield an independent determination of spent resin without having to consider the actual (total) hardness. A single ISE shown in the location of ISE 2 would also provide a clear indication of the hardness breakthrough front.

The methodology described above is capable of measuring hardness even when there is a time variant change in water hardness, such as in the case of city water feed. Hardness can be measured periodically, and preferably no less frequently than every regeneration cycle of the water softener. Time, as measured in gallons-before-regeneration may then be calculated. The user may opt not to act on any regeneration until a predetermined delta-volume of spent material is reached.

In this differential sodium measurement, it is not necessary to limit the calculations to a particular hardness ion. In fact, the methodology is independent of any particular hardness ion, e.g., calcium, iron, or magnesium, and instead presents an exact amount of total hardness.

Figure 4:
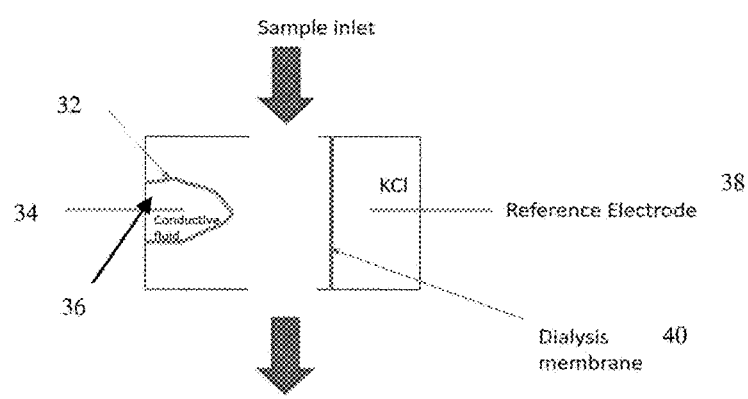
FIG. 4 is a preferred structure of an ion specific electrode (ISE) in operation.

The preferred structure of the ion specific electrode (ISE) in operation is depicted in FIG. 4.

An ionophore 32 encloses the ISE 34 within conductive fluid 36. Ionophores are a class of compounds that form complexes with specific ions and facilitate their transport across cell membranes. They are a chemical species that reversibly bind ions. Reference electrode 38 is opposite ISE 34, separated by a dialysis membrane 40. The reference electrode 38 is within a KCl solution.

Methodology Concept Verification

Initial testing has indicated that this novel sensor concept (and differential methodology) can produce accurate results. Table I lists comparative results for the disclosed embodiment of a single monovalent cation ISE over five different model inlet waters having different sodium ion concentration (and keeping the calcium concentration constant). The comparisons are made against theoretical values, EDTA standard titration, and by ISE sensor measurement. The accuracy of the EDTA method is on the order of +/−0.3 grains. The theoretical (actual) results are predicated on gravimetrically measured salts added to produce synthetic solutions.

TABLE I

| Readings | Inlet water composition $Ca^{2+}$ ppm | Inlet water composition $Na^+$ ppm | Input Total hardness (grains) (Comparative Examples-A) Theoretical | Total hardness (grains) (Comparative Examples-B) by EDTA | Total hardness (grains) (Examples) by -ISE sensor |
|---|---|---|---|---|---|
| 1 | 200 | 0 | 29.2 | 30.0 | 27.3 |
| 2 | 200 | 50 | 29.2 | 28.2 | 29.0 |
| 3 | 200 | 100 | 29.2 | 28.5 | 25.6 |
| 4 | 200 | 200 | 29.2 | 29.6 | 27.3 |
| 5 | 200 | 300 | 29.2 | 29.7 | 27.0 |

The EDTA method requires titration and is too costly and impractical to use in softeners or in other field products.

Figure 5:
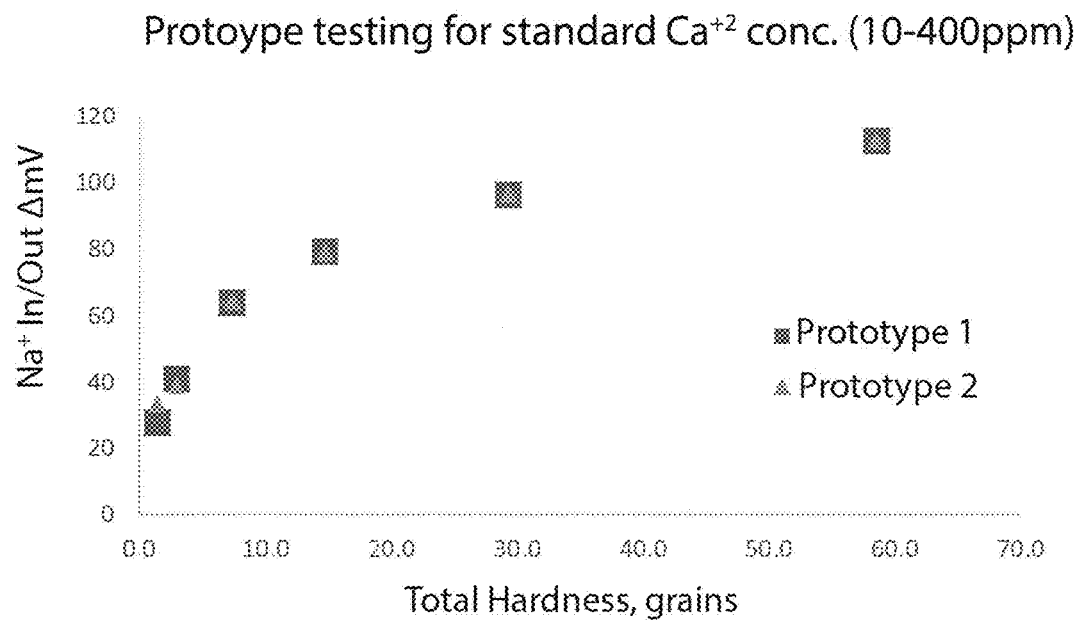
FIG. 5 depict prototype testing results of Na+ versus inflow hardness ($Ca^{+2}$ ppm)

It has become evident the preferred way to measure the hardness, which is a function of $\Delta mV$ (out–in), with minimum deviation is by using an ISE sensor. Prototype testing results of $Na^+$ versus inflow hardness ($Ca^{+2}$ ppm) is indicated in FIG. 5.

It is shown that significant variations in $Na^+$ (in/out) in $\Delta mV$ for different concentrations of $Ca^{+2}$ can be measured from a $\Delta mV$ of about 30 to about 112 for Ca' of 10 ppm to 400 ppm, respectively.

Figure 6:
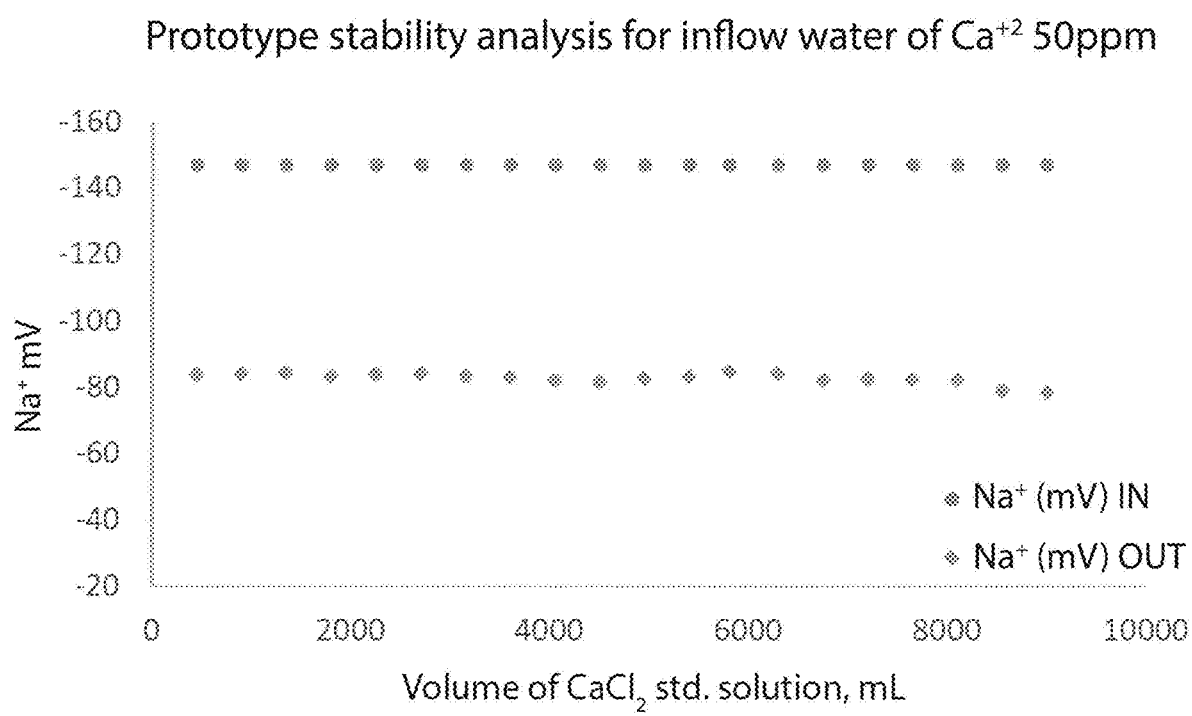
FIG. 6 depicts a graph of the measured stability of $Na^+$ in mV for inflow water over a volume range of up to about 9000 mL for $CaCl_2$ against a standard solution of $Ca^{+2}$ of 50 ppm.

Stability was also verified for each prototype over a volume of $CaCl_2$ solution. FIG. 6 depicts a graph of the measured stability of $Na^+$ in mV for inflow water over a volume range of up to about 9000 mL for $CaCl_2$ against a standard solution of $Ca^{+2}$ of 50 ppm. The flow rate was about 150 mL/min of standard solution. The outflow sampling time was every 3 minutes. No salt-leaking was observed.

Repeatability of the prototype sensor was successful, and significant variations in $\Delta mV$ for different concentrations of $Ca^{+2}$ was realized from 30 to 112 (10 ppm to 400 ppm, respectively).

Table II depicts the inflow and outflow ion concentrations for a Mass Balance relationship.

TABLE II

| Ions | In flow Concentration ppm | In flow Concentration mN | Out flow Concentration ppm | Out flow Concentration mN |
|---|---|---|---|---|
| Na | 111 | 4.83 | 322 | 14.00 |
| Ca | 134 | 6.69 | 5.5 | 0.27 |
| Mg | 38 | 3.13 | 1 | 0.08 |
| K | 11.5 | 0.29 | 3.3 | 0.08 |
| Total | | 14.93 | | 14.44 |

City water having 111 ppm Na, 134 ppm Ca, 38 ppm Mg, and 11.5 ppm K is fed into a softener. The outflow concentrations were measured at 322 ppm Na, 5.5 ppm Ca, 1 ppm Mg, and 3.3 ppm K, respectively. From these measurements, in the case of sodium, 322 ppm−111 pm=$Na_{exchanged}$=211 ppm. Thus, based on this, the calculation for the hardness removed from the feed stream: 211/7.866=26.8 grains per gallon (gpg). The total influent hardness (Ca+Mg) was found to be 28.7 gpg; however, there was some leakage of hardness through the bed, such that the actual hardness removed was 27.7 gpg, which is within 3.3% error.

TABLE III

| Ions | In flow ppm | Out flow ppm | diff. conc. ppm | mN | Na+ conc. ppm |
|---|---|---|---|---|---|
| Ca | 134 | 5.5 | 128.5 | 6.41 | 147.5 |
| Mg | 38 | 1 | 37 | 3.05 | 70.0 |
| K | 11.5 | 3.3 | 8.2 | 0.21 | 4.8 |
| Total | | | | | 222.3 |
| Na | 111 | 322 | | | 111 |
| | | | | Total | 333.3 |

In one such embodiment, a certain level of control is present. Once the total hardness is measured, a blended valve may be open until a predetermined amount of grains (hardness) is presented at the output. In this manner, precise output control of hardness may be achieved.

Feed city water with 111 ppm Na, 134 ppm Ca, 38 ppm Mg is fed into a softener. 322 ppm sodium, 5.5 ppm Ca, and 1 ppm Mg in the effluent. Thus, 322−111 ppm Na is the exchanged Sodium: $Na_{exchanged}$=211 ppm. Thus, the hardness calculated from the feed stream is: 211/7.866=26.8 grains per gallon. The total influent hardness (Ca+Mg) was found to be 28.7 grains per gallon hardness.

However, some leakage of hardness through the bed was determined. Thus, when calculating the hardness removed from the feed by the softener, it equals 27.7 grains per gallon. This represents the actual hardness removed, 27.7 gpg, while the measurement indicated that a reduced value of 26.8 gpg hardness, yielding a prediction error of 3.3%.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

The invention claimed is:

1. A method to determine a total hardness in a fluid stream comprising:
   providing an ion exchange vessel in monovalent cationic form, the ion exchange vessel having an inlet and an outlet, wherein said inlet receives a fluid stream feed of hard water;
   providing a first monovalent cation selective electrode positioned at the inlet of the ion exchange vessel to measure said hard water, and a second monovalent cation selective electrode at the outlet of the ion exchange vessel;
   measuring a first monovalent cation concentration of said fluid stream feed of hard water by a first signal output from said first monovalent cation selective electrode positioned at said inlet of said ion exchange vessel;
   measuring a second monovalent cation concentration by a second signal output from said second monovalent cation selective electrode positioned at the outlet of said ion exchange vessel;
   calculating a differential monovalent concentration; and
   calculating a first hardness value from the differential monovalent concentration.

2. The method of claim 1 including connecting the first or second monovalent cation selective electrode to a fluid path with one or more valves designed to introduce feed water or softened water to the first or second monovalent cation selective electrode.

3. The method of claim 1 including:
   mixing a fraction of hard water stream with a fraction of a softened water stream using at least one blending valve;
   calculating a subsequent hardness value with said at least one blending valve open; and
   comparing said subsequent hardness value to said first hardness value.

4. The method of claim 1 including using at least one blending valve to adjust a hardness of the fluid stream at the outlet of the ion exchange vessel.

5. The method of claim 1 wherein the first and second monovalent cation selective electrodes are selective towards cation selected from the group of elements comprising hydrogen, sodium, or potassium.

6. The method of claim 1 wherein sodium levels are monitored downstream until said sodium levels approach influent concentrations indicating a complete breakthrough of hardness.

7. The method of claim 1 wherein the second monovalent cation selective electrode at the outlet of said ion exchange vessel comprises three chambers, wherein a first chamber includes a working electrode in contact with a conductive solution and an ionophore membrane barrier, a second chamber includes a reference electrode in contact with potassium chloride (KCl) solution and bound by a dialysis membrane, and a third chamber is located between the ionophore membrane barrier and the dialysis membrane where sample fluid can be introduced for measurement, such that electrical continuity exists from said working electrode, through said conductive solution, said ionophore membrane barrier, said sample fluid, said dialysis membrane, and said KCl solution, to said reference electrode.

8. A method to determine a total hardness in a fluid stream comprising:
   providing an ion exchange vessel in monovalent cationic form, the ion exchange vessel having an inlet and outlet, wherein a fluid stream feed water of hard water is connected to the inlet of the ion exchange vessel;
   measuring in-situ monovalent cation concentration of said fluid stream feed water of hard water from a signal output of a monovalent cation selective electrode positioned at the inlet of the ion exchange vessel;
   employing a valve mechanism to redirect fluid flow, such that said valve mechanism directs said fluid stream feed water of hard water to said monovalent cation selective electrode for a first sodium measurement, and directs softened water to said monovalent cation selective electrode for a second sodium measurement;
   determining an influent hardness by measuring in-situ a differential monovalent cation concentration; and
   adjusting a hardness of the fluid stream at the outlet of the ion exchange vessel.

9. The method of claim 8, wherein the valve mechanism includes one or more valves, and the method further includes connecting the monovalent cation selective electrode to a fluid path within the one or more valves designed to introduce the fluid stream feed water or the softened water to the monovalent cation selective electrode.

10. The method of claim 8 including mixing a fraction of hard water with a fraction of a stream of said softened water using at least one blending valve in the ion exchange vessel.

11. A method for controlling hardness in a fluid stream comprising:
  introducing an ion exchange vessel in monovalent cationic form, the ion exchange vessel having an inlet and an outlet, wherein the inlet receives a fluid stream feed of hard water;
  providing a first monovalent cation selective electrode positioned at the inlet of the ion exchange vessel to measure said hard water, and a second monovalent cation selective electrode at the outlet of the ion exchange vessel;
  performing a first sodium measurement on an influent fluid stream ($Na^+_{in\text{-}initial}$); performing a second sodium measurement on an effluent fluid stream ($Na^+_{out\text{-}initial}$);
  measuring a differential monovalent concentration from said first and second sodium measurements;
  determining a total hardness value (TH) proportional to said influent fluid stream via said differential monovalent concentration such that $Na^+_{out\text{-}initial} - Na^+_{in\text{-}initial} \propto TH$;
  performing a third sodium measurement ($Na^+_{out\text{-}blend}$) downstream of a blending valve, said blending valve blending said influent fluid stream with said effluent fluid stream;
  determining an amount of total hardness removed ($TH_{removed}$) from a differential measurement of the third sodium measurement ($Na^+_{out\text{-}blend}$) and the first sodium measurement on the influent fluid stream ($Na^+_{in\text{-}initial}$) such that $Na^+_{out\text{-}blend} - Na^+_{in\text{-}initial} \propto TH_{removed}$; and
  calculating hardness in the effluent fluid stream ($H_{effluent}$) from a difference of the total hardness (TH) and the total hardness removed ($TH_{removed}$) such that $H_{effluent} = TH - TH_{removed}$.

12. The method of claim 11 further including controlling said blending valve to adjust blending of said influent fluid stream with said effluent fluid stream.

13. A method of determining regeneration of a water softener comprising:
  introducing an ion exchange vessel in monovalent cationic form, the ion exchange vessel having an inlet and an outlet, wherein the inlet receives a fluid stream feed of hard water;
  providing a first monovalent cation selective electrode positioned at the inlet of the ion exchange vessel to measure said hard water;
  measuring a first hardness value from said first monovalent cation selective electrode;
  providing a second monovalent cation selective electrode positioned within the ion exchange vessel of said water softener;
  measuring a second hardness value from said second monovalent cation selective electrode;
  calculating a differential monovalent concentration from said first and second hardness values measured; and
  determining a regeneration limit of a resin bed in said ion exchange vessel of said water softener based on the calculated differential monovalent concentration.

14. The method of claim 13 further including locating a point of consumed resin in said water softener.

15. The method of claim 13 further including determining a breakthrough measurement point to yield a determination of spent resin without measuring total (actual) hardness.

16. The method of claim 13 including predicting future regeneration by calculating time from said regeneration limit, as measured in gallons-before-regeneration.

* * * * *

UNITED STATES PATENT AND TRADEMARK OFFICE
CERTIFICATE OF CORRECTION

PATENT NO. : 11,209,413 B2  
APPLICATION NO. : 16/369682  
DATED : December 28, 2021  
INVENTOR(S) : Malcolm Kahn, Robert Astle and Jeffrey Zimmerman Page 1 of 1

It is certified that error appears in the above-identified patent and that said Letters Patent is hereby corrected as shown below:

In the Specification

Column 7, Line 3, delete "$Ba^{2+2}$" and substitute therefor -- "$Ba^{+2}$" --

Column 11, Line 8, (before Table III) add "Table III depicts the calculations of Na concentration from a difference in concentration between inflow and outflow."

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*